United States Patent [19]

Buren et al.

[11] Patent Number: 4,695,314

[45] Date of Patent: Sep. 22, 1987

[54] S-BENZYL THIOLCARBAMATES AND THEIR USE IN CONTROLLING WEEDS IN RICE FIELDS

[75] Inventors: Lawrence L. Buren, Cupertino; Donald R. James, El Sobrante; Barney J. Randolph, San Jose; Eugene G. Teach; Harry Tilles, both of El Cerrito; Francis H. Walker, Mill Valley, all of Calif.

[73] Assignee: Stauffer Chemical Company, Westport, Conn.

[21] Appl. No.: 856,270

[22] Filed: Apr. 28, 1986

Related U.S. Application Data

[63] Continuation of Ser. No. 607,106, May 3, 1984.

[51] Int. Cl.$^4$ ................. A01N 37/00; C07C 155/02
[52] U.S. Cl. ........................... 71/100; 558/242
[58] Field of Search ................. 558/242; 71/100

[56] References Cited

U.S. PATENT DOCUMENTS 3,742,005  6/1973  Tilles .................. 538/242

Primary Examiner—Henry R. Jiles
Assistant Examiner—Robert C. Whittenbaugh
Attorney, Agent, or Firm—Paul R. Martin; M. Henry Heines

[57] ABSTRACT

Novel S-benzyl thiolcarbamates are disclosed, having the formula

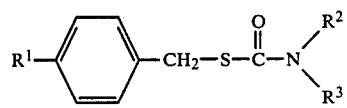

in which
$R^1$ is selected from the group consisting of hydrogen and methoxy,
$R^2$ is selected from the group consisting of methyl, ethyl, and allyl, and
$R^3$ is selected from the group consisting of straight-chain $C_3$–$C_6$ alkyl optionally substituted with one or two methyl groups, and allyl.

The compounds are particularly effective in the control of weeds associated with rice crops.

4 Claims, No Drawings

S-BENZYL THIOLCARBAMATES AND THEIR USE IN CONTROLLING WEEDS IN RICE FIELDS

This is a continuation of application Ser. No. 607,106, filed May 3, 1984.

BACKGROUND OF THE INVENTION

1. Field of the Invention

The inhibition of crop growth by weeds and other vegetation which consume valuable acreage or soil nutrients is a recurring problem in agriculture. To combat this problem, an extensive variety of chemicals and chemical formulations have been produced for application as herbicides. Many types of herbicides are disclosed in the literature and a large number are in commercial use.

Prominent among the herbicides are the thiolcarbamates, several closely related analogs of which are well established in commercial use. The present invention resides in the discovery of a novel class of thiolcarbamates, i.e., certain S-benzyl thiolcarbamates, which display unusually strong effectiveness in controlling weeds without harming the crop itself.

2. Description of the Prior Art

S-Benzyl thiolcarbamates are known as herbicidal agents in general. References disclosing such compounds include U.S. Pat. Nos. 3,679,726 (Kudamatsu et al., July 25, 1972), 3,144,475 (Harman et al., Aug. 11, 1964), 3,682,616 (Kimura et al., Aug. 8, 1972), 3,781,440 (Marco et al., Dec. 25, 1973), 3,992,185 (D'Amico, Nov. 16, 1976), 4,153,444 (Jikihara et al., May 8, 1979), 3,742,005 (Tilles, June 26, 1973), 3,582,314 (Konnai et al., June 1, 1971), and 3,930,838 (Pellegrini et al., Jan. 6, 1976), Ger. Offen. 2,138,017 (Aya et al., Feb. 3, 1972).

SUMMARY OF THE INVENTION

It has now been discovered that a certain class of S-benzyl thiolcarbamates display unusual activity in the control of weeds associated with rice crops. This class of compounds is defined by the following formula

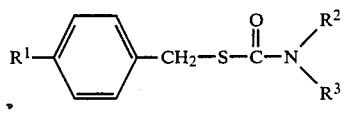

in which
$R^1$ is selected from the group consisting of hydrogen and methoxy,
$R^2$ is selected from the group consisting of methyl, ethyl, and allyl, and
$R^3$ is selected from the group consisting of straight-chain $C_3$-$C_6$ alkyl optionally substituted with one or two methyl groups, and allyl.

Within the scope of the present invention, certain embodiments are preferred, namely those in which
$R^1$ is selected from the group consisting of hydrogen and methoxy,
$R^2$ is selected from the group consisting of methyl, ethyl, and allyl, and
$R^3$ is selected from the group consisting of n-butyl, n-pentyl, 1,2-dimethylpropyl, and allyl.

DETAILED DESCRIPTION OF THE INVENTION

S-Benzyl thiolcarbamates within the scope of the present invention can be prepared by any of the known techniques for thiolcarbamate manufacture. These include the reaction between a benzyl chlorothiolformate, a secondary amine, and a base; the reaction between a carbamyl chloride and a benzyl mercaptan: and the reaction between a secondary amine, carbonyl sulfide, and a base, to form an intermediate which is in turn reacted with a benzyl halide or sulfate.

The following are examples of the preparation of several compounds within the scope of the invention, followed by demonstrations of their efficacy in the control of weeds in rice fields.

EXAMPLE 1

S-Benzyl Ethyl-1,2-dimethylpropylthiolcarbamate

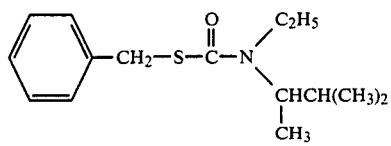

A reaction vessel was charged with 6.1 g (0.053 mole) of ethyl 1,2-dimethylpropyl amine, 5.6 g (0.055 mole) of triethylamine, and 75 ml of benzene. Once the amines were dissolved, the mixture was cooled to 0° C. A solution of 9.3 g (0.050 mole) of benzyl chlorothiolformate in 25 ml of benzene was separately prepared and added in portions to the amine mixture. The temperature rose to approximately 40° C. during the addition and a precipitate formed (triethylamine hydrochloride). After standing for several hours at room temperature, the mixture was filtered to remove the precipitate. The filtrate was washed with successive portions of 10% hydrochloric acid and water, then dried with magnesium sulfate. The solvent was then evaporated on a rotary evaporator under vacuum to yield 12.1 g (91% yield) of a liquid with refractive index $n_D^{30} = 1.5344$, confirmed by infrared spectroscopy as S-benzyl ethyl-1,2-dimethylpropylthiolcarbamate.

EXAMPLE 2

S-Benzyl Ethyl-n-butylthiolcarbamate

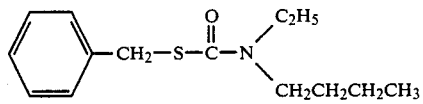

The procedure of Example 1 was followed, using 6.4 g (0.063 mole) of ethyl n-butyl amine, 6.7 g (0.066 mole) of triethylamine, and 11.2 g (0.060 mole) of benzyl chlorothiolformate. Evaporation of the solvent yielded 13.1 g (87% yield) of a liquid with refractive index $n_D^{30} = 1.5367$, confirmed by infrared spectroscopy as S-benzyl ethyl-n-butylthiolcarbamate.

EXAMPLE 3

S-Benzyl Methyl-n-pentylthiolcarbamate

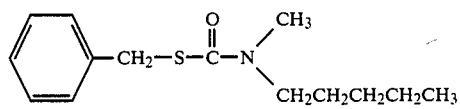

A reaction vessel was charged with 10.6 g (0.105 mole) of methyl-n-pentylamine, 11.1 g (0.11 mole) of triethylamine, and 200 ml of diethyl ether. The flask and contents were then placed in an ice bath. Over a five-minute period, 18.6 g (0.10 mole) of benzyl chlorothiolformate were added through a dropper. The flask and contents were then removed from the ice bath, and heat was applied to reflux the reaction mixture at 36° C. for thirty minutes. The mixture was cooled to room temperature and filtered to remove precipitated matter. The filtrate was washed with dilute hydrochloric acid and water and dried over magnesium sulfate, and the solvent was removed on a rotary evaporator under vacuum, and the residue was distilled in a falling film still at 165° C. to yield 19.5 g (77.7%) of a liquid, with refractive index $n_D^{30}=1.5376$, confirmed by mass spectroscopy as S-benzyl methyl-n-pentylthiolcarbamate.

EXAMPLE 4

S-Benzyl Ethyl-n-pentylthiolcarbamate

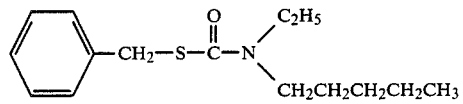

The procedure of Example 3 was followed, using 12.1 g (0.105 mole) of ethyl-N-pentylamine, 11.1 (0.11 mole) of triethylamine, 200 ml of diethyl ether, and 18.6 g (0.10 mole) of benzyl chlorothiolformate. The liquid remaining after evaporation of the solvent was distilled in a falling film still at 165° C. to produce a distillate weighing 23.5 g (88.8% yield), with refractive index $n_D^{30}=1.5326$, confirmed by mass spectroscopy as S-benzyl ethyl-n-pentylthiolcarbamate.

EXAMPLE 5

S-p-Methoxybenzyl Diallylthiolcarbamate

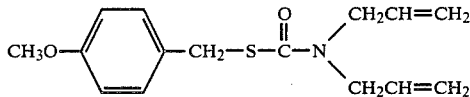

The procedure of Example 1 was followed, using 3.0 g (0.03 mole) of diallylamine, 3.1 g (0.03 mole) of triethylamine, 50 ml of benzene, and 6.5 g (0.03 mole) of p-methoxybenzylchlorothiolformate. A liquid product weighing 7.6 g (91% yield) with refractive index $n_D^{30}=1.5380$ was achieved, confirmed by infrared spectroscopy as S-p-methoxybenzyl diallylthiolcarbamate.

EXAMPLE 6

S-Benzyl Methyl-n-butylthiolcarbamate

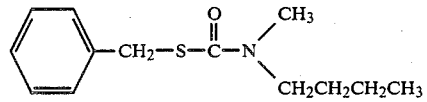

A stirred suspension of 4.7 g (0.054 mole) of methyl-n-butylamine in 100 ml of water containing 2.2 g (0.054 mole) of sodium hydroxide was treated with 10 g (0.054 mole) of benzyl chlorothiolformate, the latter added rapidly in dropwise manner. During the addition and for an hour thereafter, the mixture was stirred constantly and held to a temperature of 0°-10° C. by external cooling. To the mixture was then added 100 ml of diethyl ether. The liquid layers were then separated and the ether layer was dried over magnesium sulfate. The solvent was then evaporated to yield 11.45 g of a colorless liquid, determined by gas-liquid chromatography to be 97% pure product.

The above compounds are summarized in the following table:

TABLE I
COMPOUNDS AND REFRACTIVE INDICES

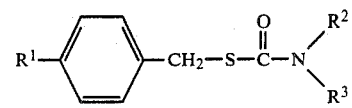

| Compound No. | $R^1$ | $R^2$ | $R^3$ | $n_D30$ |
|---|---|---|---|---|
| 1 | H | —$C_2H_5$ | $CH_3$<br>$\|$<br>—CHCH($CH_3$)$_2$ | 1.5344 |
| 2 | H | —$C_2H_5$ | —$C_4H_9$—n | 1.5367 |
| 3 | H | —$CH_3$ | —$C_5H_{11}$—n | 1.5376 |
| 4 | H | —$C_2H_5$ | —$C_5H_{11}$—n | 1.5326 |
| 5 | $CH_3O$— | allyl | allyl | 1.5380 |
| 6 | H | —$CH_3$ | —$C_4H_9$—n | — |

EXAMPLE 7

Greenhouse Tests—Post-Emergence Post-Flood Application

This example illustrates the herbicidal activity of the six compounds listed above in the control of several broadleaf and grass weed species commonly associated with rice crops. The effect of the compounds on a rice crop grown adjacent to the weeds is also observed. Simulations of flooded rice paddies were used for this test. The weed species were planted at intervals predetermined to provide a uniform degree of maturity when the test compounds were applied. Both direct seeded and transplanted rice were used to represent common growing techniques. The procedure was as follows:

Plastic tubs measuring 11.1 inches (28.2 cm) in length, 6.7 inches (17.0 cm) in width, and 5.3 inches (13.5 cm) in depth were lined with plastic and filled to a depth to 2–3 inches (5.1–7.6 cm) with sandy loam soil containing 50 parts per million by weight (ppm) of cis-N-[(trichloromethyl)thio]-4-cyclohexene-1,2-dicarboximide (a commercial fungicide known as "Captan") and 17-17-17 (percentages of N-$P_2O_5$-$K_2O$ on a weight basis) fertilizer. The weed and rice species wre then planted in each tub as follows:

1st day: Seeds of sprangletop (*Leptochloa dubia*) were planted in a single furrow.

5th day: Seeds of M-9 rice (*Oryza sativa*), sesbania (*Sesbania exaltata*), and yellow nutsedge (*Cyperus esculentus*), and cuttings of dayflower (*Commelina communis*) were planted in separate furrows. Additional seeds of M-9 rice were planted in a separate tub.

12th day: Seeds of annual morning glory (*Ipomoea purpurea*) and watergrass (*Echinochloa crusgalli*) were planted in further furrows in the tub containing the other weeds.

16th day: Rice plants grown in the separate tub were transplanted into the tub containing all the other species.

On the 20th day, the soil in each tub was flooded under 2–3 inches (5.1–7.6 cm) of water. The watergrass was in the two-leaf stage by this time and was completely submerged by the water. The other weed species and the two rows of rice were all at the water line or slightly above. The test compounds were then added on the same day to the flood water from stock solutions made by dissolving 88 mg of test compound in 40 ml acetone containing 0.1% (by weight) of a polyoxyethylene sorbitan monolaurate surface-active agent. Aliquots of the appropriate amount of solution were used to provide an application rate ranging from 0.125 to 4.0 pounds of active ingredient per acre (0.14 to 4.48 kilograms per hectare) in equivalent terms.

The water level was then maintained in each tub for three weeks, at which time each species was evaluated for percent injury. The evaluation was a visual rating comparing the treated plants to untreated plants grown under otherwise identical conditions in a separate tub. The ratings ranged from 0 to 100%, with 0 representing no injury and 100% representing complete kill. The injury ratings represented total plant injury due to all factors. The results are shown in Table II.

EXAMPLE 8

Greenhouse Tests—Pre-Emergence Surface Application

In this series, the same six test compounds were applied to dry soil after the planting of the weeds and rice, according to the following procedure:

Silty clay soil containing neither fungicide nor fertilizer was placed in plastic tubs measuring 12.0 inches (30.5 cm) by 14 inches (35.6 cm) to a depth of 4 inches (10.2 cm). Seeds of watergrass, yellow nut-sedge, and M-9 rice were planted in individual rows and the soil surface was watered lightly. Solutions of the test compounds in acetone containing the surface-active agent, ranging from 150 to 450 mg of active ingredient per 50 ml of solution were then prepared. Appropriately selected solutions were sprayed over the soil surface by the use of a linear spray table at a spray rate corresponding to 80 gallons per acre (750 liters per hectare) to achieve application rates equivalent to 2 to 6 pounds of active ingredient per acre (2.2 to 6.7 kilograms per hectare).

Two weeks later, an additional row of watergrass seeds was planted, and an additional two weeks later, a third row was planted. These two late plantings were done in order to test the residual activity of the test compounds. The tubs were watered regularly.

TABLE II

GREENHOUSE HERBICIDE TEST RESULTS
POST-EMERGENCE, POST-FLOOD APPLICATION

| Test Compound No. | Application Rate (lb/A) | Percent Injury | | | | | | Rice | |
|---|---|---|---|---|---|---|---|---|---|
| | | Morning-glory | Ses-bania | Nut-sedge | Water-grass | Sprangle-top | Day-flower | Direct Seeded | Trans-planted |
| 1 | 0.125 | 0 | 0 | 0 | 0 | 0 | 0 | 0 | 0 |
| | 0.25 | 0 | 0 | 0 | 50 | 0 | 0 | 0 | 0 |
| | 0.5 | 90 | 0 | 20 | 100 | 100 | 0 | 20 | 20 |
| | 1.0 | 90 | 10 | 85 | 100 | 100 | 0 | 35 | 35 |
| | 2.0 | 90 | 20 | 85 | 100 | 100 | 50 | 50 | 50 |
| | 4.0 | 100 | 75 | 95 | 100 | 100 | 95 | 75 | 75 |
| 2 | 0.125 | 0 | 0 | 0 | 0 | 0 | 0 | 0 | 0 |
| | 0.25 | 0 | 0 | 0 | 20 | 95 | 0 | 0 | 0 |
| | 0.5 | 100 | 0 | 0 | 95 | 95 | 0 | 10 | 0 |
| | 1.0 | 100 | 0 | 25 | 100 | 100 | 0 | 20 | 10 |
| | 2.0 | 100 | 75 | 95 | 100 | 100 | 95 | 20 | 20 |
| | 4.0 | 100 | 100 | 100 | 100 | 100 | 100 | 85 | 85 |
| 3 | 0.125 | 0 | 0 | 0 | 0 | 0 | 0 | 0 | 0 |
| | 0.25 | 0 | 0 | 0 | 25 | 50 | 0 | 0 | 0 |
| | 0.5 | 0 | 0 | 0 | 95 | 50 | 0 | 0 | 0 |
| | 1.0 | 0 | 0 | 0 | 100 | 95 | 0 | 0 | 0 |
| | 2.0 | 0 | 0 | 0 | 100 | 100 | 0 | 0 | 0 |
| | 4.0 | 0 | 0 | 85 | 100 | 100 | 0 | 40 | 0 |
| 4 | 0.125 | 0 | 0 | 0 | 0 | 0 | 0 | 0 | 0 |
| | 0.25 | 0 | 0 | 0 | 40 | 95 | 0 | 0 | 0 |
| | 0.5 | 100 | 0 | 0 | 100 | 95 | 0 | 0 | 0 |
| | 1.0 | 100 | 0 | 60 | 100 | 100 | 0 | 0 | 0 |
| | 2.0 | 100 | 0 | 60 | 100 | 100 | 0 | 0 | 0 |
| | 4.0 | 100 | 0 | 60 | 100 | 100 | 20 | 10 | 10 |
| 5 | 0.125 | 0 | 0 | 0 | 10 | 0 | 0 | 0 | 0 |
| | 0.25 | 0 | 0 | 0 | 60 | 0 | 0 | 0 | 0 |
| | 0.5 | 0 | 0 | 0 | 100 | 0 | 0 | 0 | 0 |
| | 1.0 | 100 | 0 | 0 | 100 | 20 | 0 | 0 | 0 |
| | 2.0 | 100 | 0 | 0 | 100 | 100 | 0 | 0 | 0 |
| | 4.0 | 100 | 0 | 100 | 100 | 100 | 0 | 10 | 10 |
| 6 | 0.125 | 0 | 0 | 0 | 0 | 0 | 0 | 0 | 0 |
| | 0.25 | 0 | 0 | 0 | 0 | 0 | 0 | 0 | 0 |
| | 0.5 | 0 | 0 | 0 | 50 | 0 | 0 | 0 | 0 |
| | 1.0 | 100 | 20 | 0 | 100 | 95 | 0 | 0 | 0 |
| | 2.0 | 100 | 40 | 0 | 100 | 100 | 0 | 10 | 20 |
| | 4.0 | 100 | 40 | 20 | 100 | 100 | 0 | 20 | 20 |

Three weeks after the last watergrass seeds were planted, injury ratings of each plant species were taken as in Example 6. The results are shown in Table III.

TABLE III

GREENHOUSE HERBICIDE TEST RESULTS
PRE-EMERGENCE SURFACE APPLICATION

| Test Compound No. | Application Rate (lb/A) | Nutsedge | Percent Injury Watergrass - Seeding Date Day of Application | 2 Weeks | 4 Weeks | Rice |
|---|---|---|---|---|---|---|
| 1 | 2 | 10 | 98 | 0 | 0 | 0 |
|   | 4 | 20 | 100 | 0 | 0 | 0 |
|   | 6 | 40 | 100 | 0 | 0 | 0 |
| 2 | 2 | 0 | 50 | 0 | 0 | 0 |
|   | 4 | 20 | 50 | 0 | 0 | 10 |
|   | 6 | 20 | 100 | 0 | 0 | 20 |
| 3 | 2 | 0 | 0 | 0 | 0 | 0 |
|   | 4 | 0 | 50 | 0 | 0 | 0 |
|   | 6 | 0 | 80 | 0 | 0 | 0 |
| 4 | 2 | 0 | 0 | 0 | 0 | 0 |
|   | 4 | 10 | 80 | 0 | 0 | 0 |
|   | 6 | 10 | 90 | 25 | 0 | 0 |
| 5 | 2 | 0 | 50 | 0 | 0 | 0 |
|   | 4 | 10 | 90 | 20 | 10 | 20 |
|   | 6 | 20 | 100 | 90 | 95 | 25 |
| 6 | 2 | 0 | 50 | 0 | 0 | 0 |
|   | 4 | 10 | 50 | 10 | 0 | 15 |
|   | 6 | 10 | 50 | 20 | 0 | 25 |

EXAMPLE 9

Outdoor Tests—Post-Emergence, Post-Flood Application

In this series, four of the compounds were tested in outdoor tubs following a procedure similar to that described in Example 7 above. This series covers various stages in the growth of both rice and watergrass.

Plastic tubs which were 16.0 inches (40.6 cm) in diameter and 8.5 inches (21.6 cm) deep were filled to a depth of 3.0 inches (7.6 cm) with sandy loam soil containing 50 ppm each of the same fungicide and fertilizer used in the tests in Example 7. The seeding plan was as follows:

1st day: Seeds of yellow nutsedge and sprangle top were planted.
5th day: Seeds of red rice (a weed species) and M-9 rice were planted. Additional M-9 rice seeds were planted in a separate tub for later transplanting.
7th day: Dayflower cuttings were planted.
12th day: Seeds of watergrass and M-9 rice were planted.
16th day: Seeds of sesbania, watergrass, and M-9 rice were planted.
19th day: Seeds of watergrass and M-9 rice were planted.
25th day: The separately grown rice plants were transplanted to the main tub.

On the 27th day, the tubs were flooded to achieve a water depth of 5.0 inches (12.7 cm), and aliquots of test compound solutions in acetone containing the surface-active agent were added to the flood water to provide application rates equivalent to 0.5 to 4.0 pounds of active ingredient per acre (0.56 to 4.48 kilograms per hectare) (18.4 mg per tub is equivalent to 1 pound per acre). At this point, the dayflower plants were about 90% submerged, the sesbania were 2 inches (5.1 cm) tall with primary leaves, secondary growth beginning to appear, the sprangletop showed sporadic growth averaging 6 inches (15.2 cm) in height, the red rice plants were 7 to 8 inches (17.8–20.3 cm) tall, and the nutsedge were just above the water level. Due to cold weather, the sprangletop in several of the tubs failed to germinate. The watergrass in its several separate plantings ranged from the two-leaf stage (1–2 inches or 2.5–5.1 cm tall) to the four-leaf stage (7–9 inches or 17.8–22.9 cm tall). The M-9 rice ranged from the one-leaf stage (1–2 inches or 2.5–5.1 cm tall) to the three-leaf stage (5–7 inches or 12.7–17.8 cm tall).

The results are shown in Table IV.

TABLE IV

OUTDOOR HERBICIDE TEST RESULTS
POST EMERGENCE, POST-FLOOD APPLICATION

| Application Rate (lb/A) | Sprangle top | Red Rice | Sesbania | Nutsedge | Dayflower | Watergrass Days 15 | 11 | 8 | M-9 Rice: Days 18 | 15 | 11 | 8 | Transplanted |
|---|---|---|---|---|---|---|---|---|---|---|---|---|---|
| Test Compound No. 2: | | | | | | | | | | | | | |
| 0.5 | 0 | 0 | 0 | 0 | 0 | 0 | 100 | 50 | 0 | 0 | 0 | 50 | 0 |
| 1.0 | 100 | 0 | 0 | 0 | — | 20 | 100 | 95 | 0 | 0 | 0 | 50 | 0 |
| 2.0 | — | 10 | 100 | 10 | 90 | 100 | 100 | — | 0 | 0 | 50 | 90 | 0 |
| 4.0 | — | 20 | 100 | 90 | 100 | 100 | 100 | — | 20 | 20 | 90 | — | 0 |
| Test Compound No. 3: | | | | | | | | | | | | | |
| 0.5 | 0 | 0 | 0 | 0 | 0 | 0 | 0 | — | 0 | 0 | 0 | 0 | 0 |
| 1.0 | 100 | 0 | 0 | 0 | 0 | 50 | — | — | 0 | 0 | 0 | 0 | 0 |
| 2.0 | 100 | 0 | 100 | 0 | 95 | 90 | 100 | — | 0 | 0 | 0 | 0 | 0 |
| 4.0 | 100 | 0 | 100 | 20 | 100 | 90 | 100 | — | 0 | 0 | 0 | 0 | 0 |
| Test Compound No. 4: | | | | | | | | | | | | | |
| 0.5 | 0 | 0 | 0 | 0 | 0 | 0 | 100 | —* | 0 | 0 | 0 | 0 | 0 |
| 1.0 | 0 | 0 | 0 | 0 | 0 | 50 | 100 | — | 0 | 0 | 0 | 0 | 0 |
| 2.0 | 100 | 0 | 0 | 0 | 0 | 85 | 100 | — | 0 | 0 | 0 | 0 | 0 |
| 4.0 | 100 | 0 | 0 | 20 | 95 | 95 | 100 | 100 | 0 | 0 | 0 | 0 | 0 |
| Test Compound No. 5: | | | | | | | | | | | | | |
| 0.5 | — | 0 | 0 | 0 | 0 | 0 | 0 | — | 0 | 0 | 0 | 0 | 0 |
| 1.0 | — | 0 | 0 | 0 | 0 | 10 | 100 | — | 0 | 0 | 0 | 0 | 0 |
| 2.0 | — | 0 | 0 | 0 | 90 | 20 | 90 | 90 | 0 | 0 | 0 | 0 | 0 |
| 4.0 | — | 100 | 90 | 95 | 90 | 100 | — | — | 0 | 0 | 0 | 0 | 0 |

EXAMPLE 10

Outdoor Tests—Post-Emergence, Post-Flood Application

This series is similar to that of Example 9, except that all six test compounds shown in Table I were tested. The seeding plan was as follows:
1st day: Yellow nutsedge seeds were planted.
2nd day: Dayflower cuttings were planted.
14th day: Sesbania seeds were planted.
19th day: Red rice and M-9 rice seeds were planted. Additional red rice seeds were planted in a separate tub for later transplanting.
22nd day: Watergrass and M-9 rice seeds were planted.
24th day: Watergrass seeds were planted.
26th day: Watergrass seeds were planted.
28th day: Watergrass seeds were planted.
33rd day: The separately grown rice plants were transplanted to the main tub.

Flooding and treatment with the test compounds were done on the 37th day and injury ratings were taken four weeks later. The results are shown in Table V.

TABLE V

OUTDOOR HERBICIDE TEST RESULTS
POST-EMERGENCE, POST-FLOOD APPLICATION

| Test Compound No. | Application Rate (lb/A) | Red Rice | Sesbania | Nutsedge | Dayflower | Percent Injury Watergrass Days 15 | 13 | 11 | 9 | M-9 Rice: Days 18 | 15 | Transplanted |
|---|---|---|---|---|---|---|---|---|---|---|---|---|
| 1 | 1.0 | 0 | 0 | 0 | 0 | 75 | 75 | 0 | 0 | 0 | 0 | 0 |
|   | 1.0 | 0 | 0 | 0 | 0 | 40 | 60 | 0 | 0 | 0 | 0 | 0 |
|   | 2.0 | 0 | 0 | 0 | 0 | 50 | 50 | 100 | 100 | 0 | 0 | 0 |
|   | 2.0 | 0 | 0 | 0 | 0 | 90 | 90 | 100 | 100 | 0 | 0 | 0 |
|   | 3.0 | 0 | 90 | 0 | 90 | 75 | 75 | 100 | 100 | 0 | 0 | 0 |
|   | 3.0 | 0 | 95 | 0 | 90 | 80 | 95 | 100 | 100 | 0 | 0 | 0 |
|   | 4.0 | 0 | 95 | 0 | 90 | 100 | 100 | 100 | 100 | 15 | 15 | 0 |
|   | 4.0 | 0 | 95 | 0 | 90 | 100 | 100 | 100 | 100 | 20 | 20 | 0 |
| 2 | 1.0 | 0 | 0 | 0 | 0 | 0 | 0 | 0 | 0 | 0 | 0 | 0 |
|   | 1.0 | 0 | 0 | 0 | 0 | 0 | 75 | 0 | 0 | 0 | 0 | 0 |
|   | 2.0 | 0 | 0 | 0 | 0 | 20 | 75 | 100 | 100 | 0 | 0 | 0 |
|   | 2.0 | 0 | 0 | 0 | 0 | 75 | 100 | 100 | 100 | 0 | 0 | 0 |
|   | 3.0 | 0 | 0 | 0 | 0 | 100 | 100 | 100 | 100 | 0 | 0 | 0 |
|   | 3.0 | 0 | 0 | 0 | 0 | 95 | 100 | 100 | 100 | 0 | 0 | 0 |
|   | 4.0 | 10 | 0 | 0 | 0 | 100 | 100 | 100 | 100 | 5 | 5 | 10 |
|   | 4.0 | 10 | 0 | 0 | 0 | 95 | 100 | 100 | 100 | 10 | 10 | 10 |
|   | 6.0 | 10 | 0 | 0 | 0 | 100 | 100 | 100 | 100 | 10 | 10 | 10 |
|   | 6.0 | 10 | 0 | 0 | 0 | 100 | 100 | 100 | 100 | 10 | 10 | 10 |
| 3 | 1.0 | 0 | 0 | 0 | 0 | 0 | 90 | 100 | 100 | 0 | 0 | 0 |
|   | 1.0 | 0 | 0 | 0 | 0 | 0 | 0 | 100 | 100 | 0 | 0 | 0 |
|   | 2.0 | 0 | 0 | 0 | 0 | 20 | 90 | 100 | 100 | 0 | 0 | 0 |
|   | 2.0 | 0 | 0 | 0 | 0 | 0 | 90 | 100 | 100 | 0 | 0 | 0 |
|   | 3.0 | 0 | 0 | 0 | 0 | 98 | 100 | 100 | 100 | 0 | 0 | 0 |
|   | 3.0 | 0 | 0 | 0 | 0 | 75 | 100 | 100 | 100 | 0 | 0 | 0 |
|   | 4.0 | 10 | 0 | 0 | 0 | 100 | 100 | 100 | 100 | 10 | 10 | 10 |
|   | 4.0 | 10 | 0 | 0 | 0 | 100 | 100 | 100 | 100 | 10 | 10 | 10 |
|   | 6.0 | 10 | 0 | 0 | 10 | 100 | 100 | 100 | 100 | 10 | 10 | 10 |
|   | 6.0 | 10 | 100 | 0 | 10 | 100 | 100 | 100 | 100 | 10 | 10 | 10 |
| 4 | 1.0 | 0 | 0 | 0 | 0 | 0 | 0 | 100 | 100 | 0 | 0 | 0 |
|   | 1.0 | 0 | 0 | 0 | 0 | 0 | 0 | 100 | 100 | 0 | 0 | 0 |
|   | 2.0 | 0 | 0 | 0 | 0 | 20 | 75 | 100 | 100 | 0 | 0 | 0 |
|   | 2.0 | 0 | 0 | 0 | 0 | 0 | 75 | 0 | 0 | 0 | 0 | 0 |
|   | 3.0 | 0 | 0 | 0 | 0 | 95 | 100 | 100 | 100 | 0 | 0 | 0 |
|   | 3.0 | 0 | 0 | 0 | 0 | 100 | 100 | 100 | 100 | 0 | 0 | 0 |
|   | 4.0 | 0 | 0 | 0 | 10 | 100 | 100 | 100 | 100 | 10 | 10 | 10 |
|   | 4.0 | 10 | 0 | 0 | 10 | 100 | 100 | 100 | 100 | 20 | 20 | 20 |
|   | 6.0 | 10 | 50 | 0 | 90 | 100 | 100 | 100 | 100 | 20 | 20 | 20 |
|   | 6.0 | 10 | 100 | 0 | 90 | 100 | 100 | 100 | 100 | 25 | 50 | 25 |
| 5 | 1.0 | 0 | 0 | 0 | 0 | 0 | 0 | 100 | 100 | 0 | 0 | — |
|   | 1.0 | 0 | 0 | 0 | 0 | 0 | 75 | 100 | 100 | 0 | 0 | — |
|   | 2.0 | 0 | 0 | 0 | 0 | 0 | 90 | 100 | 100 | 0 | 0 | — |
|   | 2.0 | 0 | 0 | 0 | 0 | 20 | 50 | 100 | 100 | 0 | 0 | — |
|   | 3.0 | 0 | 0 | 0 | 0 | 75 | 100 | 100 | 100 | 0 | 0 | — |
|   | 3.0 | 0 | 0 | 0 | 0 | 75 | 75 | 100 | 100 | 0 | 0 | — |
|   | 4.0 | 0 | 0 | 0 | 0 | 90 | 90 | 100 | 100 | 0 | 0 | — |
|   | 4.0 | 0 | 0 | 0 | 0 | 100 | 100 | 100 | 100 | 0 | 0 | — |
|   | 6.0 | 0 | 0 | 0 | 0 | 95 | 95 | 100 | 100 | 0 | 0 | — |
|   | 6.0 | 0 | 0 | 0 | 0 | 95 | 95 | 100 | 100 | 0 | 0 | — |
| 6 | 1.0 | 0 | 0 | 0 | 0 | 75 | 0 | 100 | 100 | 0 | 0 | 0 |
|   | 2.0 | 0 | 75 | 10 | 0 | 85 | 100 | 100 | 100 | 0 | 0 | 0 |
|   | 3.0 | 0 | 100 | 10 | 100 | 95 | 100 | 100 | 100 | 0 | 0 | 0 |
|   | 3.0 | 0 | 100 | 10 | 100 | 75 | 100 | 100 | 100 | 0 | 0 | 0 |
|   | 4.0 | 0 | 100 | 10 | 100 | 98 | 100 | 100 | 100 | 0 | 0 | 0 |
|   | 4.0 | 0 | 100 | 10 | 100 | 100 | 100 | 100 | 100 | 0 | 0 | 0 |
|   | 6.0 | 0 | 100 | 10 | 75 | 100 | 100 | 100 | 100 | 0 | 0 | 0 |
|   | 6.0 | 0 | 100 | 10 | 100 | 100 | 100 | 100 | 100 | 0 | 0 | 0 |

EXAMPLE 11

Greenhouse Tests—Post-Emergence, Post-Flood Application

This series of tests was run on watergrass only, focusing on the residual activity of the test compounds in water after one month.

Planting tubs identical to those used in Example 7 were planted with watergrass seeds. After one week, the tubs were flooded with treated water taken from the outdoor tubs of Example 9. Three weeks later, injury ratings were taken. The results are shown in Table VI.

TABLE VI

GREENHOUSE TEST RESULTS -
POST-EMERGENCE APPLICATION
USING PRE-TREATED FLOOD WATER
(Watergrass only)

| Application Rate (lb/A) | Percent Injury COMPOUND NO: | | | | | |
|---|---|---|---|---|---|---|
|  | 1 | 2 | 3 | 4 | 5 | 6 |
| 1.0 | 0 | 0 | 0 | 0 | 0 | 0 |
| 1.0 | 20 | 0 | 0 | 0 | 0 | — |
| 2.0 | 75 | 0 | 0 | 0 | 0 | 0 |
| 2.0 | 75 | 0 | 0 | 0 | 0 | — |
| 3.0 | 90 | 0 | 0 | 0 | 0 | 0 |
| 3.0 | 60 | 0 | 0 | 0 | 0 | 0 |
| 4.0 | 98 | 0 | 0 | 0 | 0 | 10 |
| 4.0 | 100 | 0 | 0 | 0 | 0 | 10 |
| 6.0 | — | 0 | 10 | 10 | 0 | 10 |
| 6.0 | — | 0 | 10 | 10 | 0 | 10 |

METHODS OF APPLICATION

The compounds of the present invention are useful in controlling the growth of undesirable vegetation by preemergence or post-emergence application to the locus where control is desired. The compounds are generally embodied in formulations suitable for convenient application, containing additional ingredients or diluent carriers to aid in the dispersal of the compositions. Examples of such ingredients or carriers are water, organic solvents, granules, surface active agents, water-oil emulsions, wetting agents, dispersing agents, and emulsifying agents. The formulated compositions generally take the form of emulsifiable concentrates, granules, or microcapsules.

A. EMULSIFIABLE CONCENTRATES

Emulsifiable concentrates are solutions in which the active material and an emulsifying agent are dissolved in a non-water-miscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

B. GRANULES

Granules are physically stable, particulate compositions in which the active ingredient adheres to or is distributed throughout a basic matrix of a coherent, inert carrier with macroscopic dimensions. A typical particle is about 1 to 2 millimeters in diameter. Surfactants are often present to aid in the leaching of the active ingredient from the granule to the surrounding medium.

The carrier is preferably of mineral origin, and generally falls within one of two types. The first are porous, absorptive, preformed granules, such as attapulgite or heat expanded vermiculite. A solution of the active agent is sprayed on the granule at concentrations of up to 25 weight percent of the total weight. The second are powdered materials to which the active ingredients are added prior to being formed into granules. These materials include kaolin clays, hydrated attapulgite, or bentonite clays in the form of sodium, calcium, or magnesium bentonites. Water-soluble salts may also be present to help the granules disintegrate in water. These ingredients are blended with the active components, then granulated or pelleted, followed by drying. In the resulting composition, the active component is distributed uniformly throughout the mass. Granules can be made with as much as 25 to 30 weight percent active component, but more frequently a concentration of about 10 weight percent is desired for optimum distribution. Granule compositions are most useful in a size range of 15–30 mesh.

The surfactant is generally a common wetting agent of anionic or nonionic character. The most suitable wetting agents depend upon the type of granule used. When preformed granules are sprayed with active material in liquid form, the most suitable wetting agents are nonionic, liquid wetters miscible with the solvent. These are compounds generally known as emulsifiers and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents usually comprise up to about 5 weight percent of the total composition.

When the active ingredient is first mixed with a powdered carrier and subsequently granulated, liquid nonionic wetters can still be used, but it is usually preferable to incorporate at the mixing stage a solid, powdered anionic wetting agent comprising up to about 2.0 weight percent of the total composition.

Typical granules comprise about 5 to 30 percent by weight active material, about 0 to 5 weight percent wetting agent, and about 65 to 95 weight percent carrier.

C. MICROCAPSULES

Microcapsules are fully enclosed droplets or granules in which the active material is enclosed in an inert porous membrane which allows the enclosed material to escape to the surrounding medium at controlled rates.

Encapsulated droplets are typically about 1 to 50 microns in diameter. The enclosed liquid typically constitutes about 50 to 95% of the weight of the capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

D. IN GENERAL

In general, any conventional method of application can be used. The locus of application can be soil, seeds, seedlings, or the actual plants, as well as flooded fields. Liquid compositions can be applied by the use of boom or hand sprayers. Liquid or solid compositions can be applied from airplanes. The compositions can also be added to irrigation water so that they will accompany the water as it penetrates the soil, and also to flood water in rice cultivation.

The amount of active ingredient required for herbicidal effectiveness depends upon the nature of the seeds or plants to be controlled and the prevailing conditions. Usually, herbicidal effects are obtained with an application rate of about 0.01 to about 50 pounds per acre, preferably about 0.1 to about 25. It will be readily apparent to one skilled in the art that compounds exhibiting lower herbicidal activity will require a higher dosage than more active compounds for the same degree of control.

What is claimed is:

1. S-benzyl-N-ethyl-N-1,2-dimethylpropyl thiocarbamate.

2. A herbicide composition comprising an herbicidally effective amount of S-benzyl-n-ethyl-n-1,2-dimethylpropyl thiocarbamate and an inert diluent carrier.

3. A method of controlling undesirable vegetation in rice crops comprising applying to the locus where control is desired an herbicidal composition comprising an herbicidally effective amount of S-benzyl-n-ethyl-n-1,2-dimethylpropyl thiocarbamate and an inert diluent carrier.

4. A method of controlling watergrass which comprises applying to the locus where control is desired an herbicidal composition comprising a herbicidally effective amount of S-benzyl-n-ethyl-n-1,2-dimethylpropyl thiocarbamate and an inert diluent carrier.

* * * * *